(12) United States Patent
Schwandt

(10) Patent No.: US 9,656,113 B2
(45) Date of Patent: May 23, 2017

(54) CLOTH BACK SUPPORT APPARATUS AND METHODS OF USE

(71) Applicant: Kara Marie Schwandt, Nort Vancouver (CA)

(72) Inventor: Kara Marie Schwandt, Nort Vancouver (CA)

(73) Assignee: Kara M Schwandt, North Vancouver (CA)

( * ) Notice: Subject to any disclaimer, the term of this patent is extended or adjusted under 35 U.S.C. 154(b) by 0 days.

(21) Appl. No.: 14/847,007

(22) Filed: Sep. 8, 2015

(65) Prior Publication Data

US 2016/0144215 A1 May 26, 2016

Related U.S. Application Data

(60) Provisional application No. 62/057,271, filed on Sep. 30, 2014.

(51) Int. Cl.
*A63B 21/002* (2006.01)
*A41D 23/00* (2006.01)
(Continued)

(52) U.S. Cl.
CPC .......... *A63B 21/0023* (2013.01); *A41D 15/04* (2013.01); *A41D 23/00* (2013.01);
(Continued)

(58) Field of Classification Search
CPC . A63B 21/002; A63B 21/0023; A63B 21/065; A63B 21/4003; A63B 21/4037; A63B 21/4039; A63B 2023/006; A63B 26/00; A63B 21/00178; A63B 21/4007; A63B 21/4011; A63B 21/02; A63B 2208/0228; A63B 2208/0238; A63B 2210/54; A63B 2225/09; A63B 2225/685; A63B 2225/687; A63B 2209/02; A63B 2209/10; A41D 23/00; A41D 2023/006;
(Continued)

(56) References Cited

U.S. PATENT DOCUMENTS 2,287,887 A * 6/1942 Kramer ................... A41D 23/00
2/91
3,748,661 A * 7/1973 Smith ....................... A42B 5/00
2/144
(Continued)

OTHER PUBLICATIONS

Ryder, C. [expertvillage]. (Oct. 2, 2008). Restorative Yoga Poses: Restorative Yoga Reclined Cross-Legged Pose [Video file]. Retrieved from https://www.youtube.com/watch?v=ESSznAdyTx4.*
(Continued)

*Primary Examiner* — Joshua Lee

(57) ABSTRACT

A back support apparatus which includes a length of cloth consisting of a tail, body and buckle; the tail and buckle join to form a loop inside which a user sits. The apparatus and method of use stabilize a user in a seated position. The method of use is as follows: the cloth is wrapped around the users back and knees while in a seated, crossed leg position, and the tail threaded through the buckle and cinched tight in front of the users body. The apparatus is adjusted by pulling the tail further through the buckle, increasing support, or pulling the buckle away from the user's body, releasing tension.

12 Claims, 24 Drawing Sheets

(51) Int. Cl.

| | | |
|---|---|---|
| *A45F 3/14* | (2006.01) | |
| *A61F 7/02* | (2006.01) | |
| *A41D 15/04* | (2006.01) | |
| *A63B 21/02* | (2006.01) | |
| *A63B 23/00* | (2006.01) | |
| *A63B 21/00* | (2006.01) | |

(52) U.S. Cl.
CPC ................ *A45F 3/14* (2013.01); *A61F 7/02* (2013.01); *A61F 2007/023* (2013.01); *A63B 21/00178* (2013.01); *A63B 21/02* (2013.01); *A63B 21/4007* (2015.10); *A63B 21/4011* (2015.10); *A63B 2023/006* (2013.01); *A63B 2208/0228* (2013.01); *A63B 2208/0238* (2013.01); *A63B 2209/02* (2013.01); *A63B 2209/10* (2013.01); *A63B 2210/54* (2013.01); *A63B 2225/09* (2013.01); *A63B 2225/685* (2013.01); *A63B 2225/687* (2013.01)

(58) Field of Classification Search
CPC .............. A41D 2023/008; A41D 15/04; A61H 2201/1652; A45F 3/14; A61F 7/02; A61F 2007/023
See application file for complete search history.

(56) References Cited

U.S. PATENT DOCUMENTS

| | | | | | |
|---|---|---|---|---|---|
| 4,773,106 | A  * | 9/1988 | Toso | ...................... | A47C 16/00 297/464 |
| 5,950,887 | A  * | 9/1999 | Powell | ................. | A47D 13/025 224/158 |
| 7,231,670 | B2 * | 6/2007 | Chang | .................... | A41D 23/00 2/207 |
| 8,038,584 | B1 * | 10/2011 | Pruessner | ................ | A61H 1/02 482/143 |
| 8,783,530 | B1 * | 7/2014 | Jordan | ................. | A47D 13/025 224/158 |
| 2005/0239604 | A1 * | 10/2005 | Denham | ................... | A45F 4/00 482/23 |
| 2006/0052222 | A1 * | 3/2006 | Cardenas | ............. | A61H 1/0229 482/96 |
| 2006/0157525 | A1 * | 7/2006 | Furlong | .................... | A45F 3/02 224/601 |
| 2006/0237493 | A1 * | 10/2006 | Tsai | ...................... | A47D 13/025 224/159 |
| 2006/0283205 | A1 * | 12/2006 | Carriere | ................. | A45C 13/02 62/457.2 |
| 2007/0062989 | A1 * | 3/2007 | Kassai | ................. | A47D 13/025 224/158 |
| 2007/0066467 | A1 * | 3/2007 | Edwards | .................. | A63B 6/00 482/148 |
| 2008/0116239 | A1 * | 5/2008 | Lu | ............................. | A45F 3/14 224/575 |
| 2008/0229501 | A1 * | 9/2008 | Hutchison | .............. | A45C 13/30 5/420 |
| 2009/0197747 | A1 * | 8/2009 | Chan | .................. | A63B 21/0004 482/122 |
| 2011/0131723 | A1 * | 6/2011 | Andrews | ................... | A45F 3/14 5/417 |
| 2012/0043355 | A1 * | 2/2012 | Cook | ...................... | A44B 11/04 223/83 |
| 2012/0248159 | A1 * | 10/2012 | Rahni | .................... | A47D 13/02 224/158 |
| 2013/0047316 | A1 * | 2/2013 | Gillan | .................. | A44C 15/005 2/207 |
| 2014/0069970 | A1 * | 3/2014 | Thomas, Jr. | .............. | A45F 3/14 224/257 |
| 2014/0084031 | A1 * | 3/2014 | Bowden | ................ | A47D 13/025 224/158 |
| 2014/0215687 | A1 * | 8/2014 | Andrews | ................ | A41D 23/00 2/170 |
| 2014/0272850 | A1 * | 9/2014 | Knight | .................... | G09B 19/00 434/247 |
| 2015/0189997 | A1 * | 7/2015 | Gmeiner | ................ | A47D 13/02 224/158 |

OTHER PUBLICATIONS

Aravena, A. (Apr. 15, 2010). Chairless by Alejandro Arevana for Vitra. Dezeen Magazine. Retrieved from http://www.dezeen.com/2010/04/15/chairless-by-alejandro-aravena-for-vitra/.*

Bell, C. (Mar. 26, 2012). Yoga Straps: How it All started. Retrieved from http://www.huggermugger.com/blog/2012/yoga-straps/.*

* cited by examiner

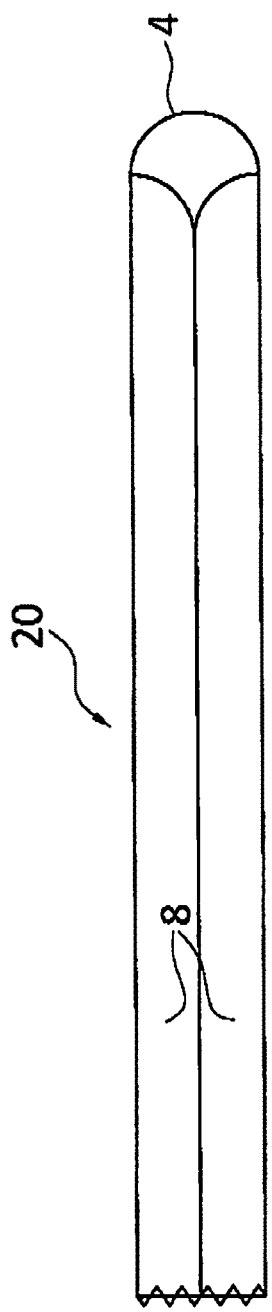

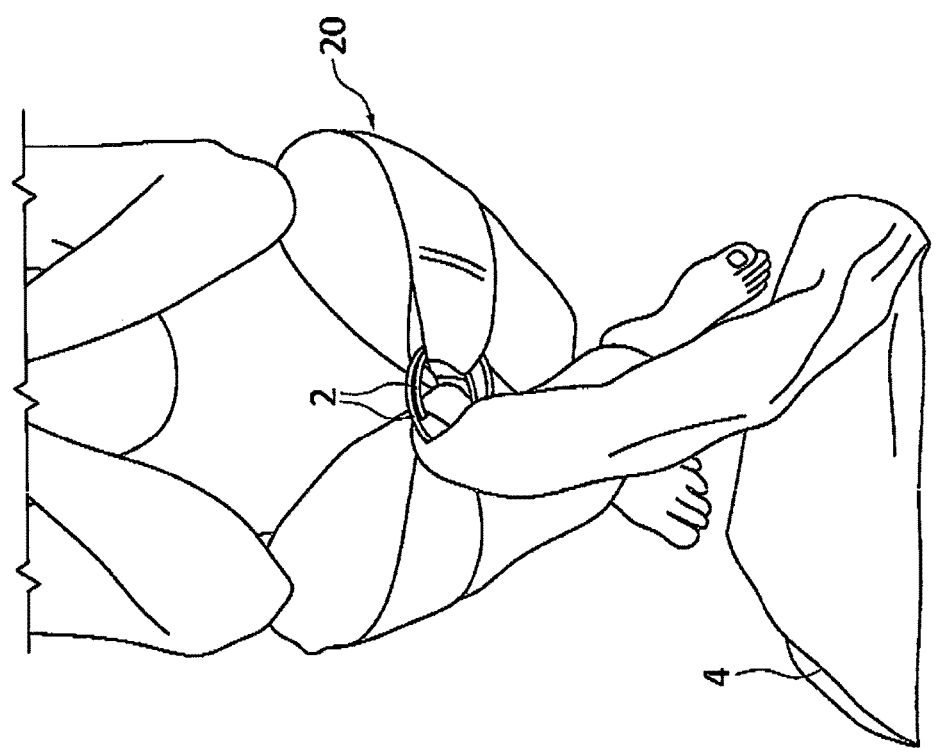

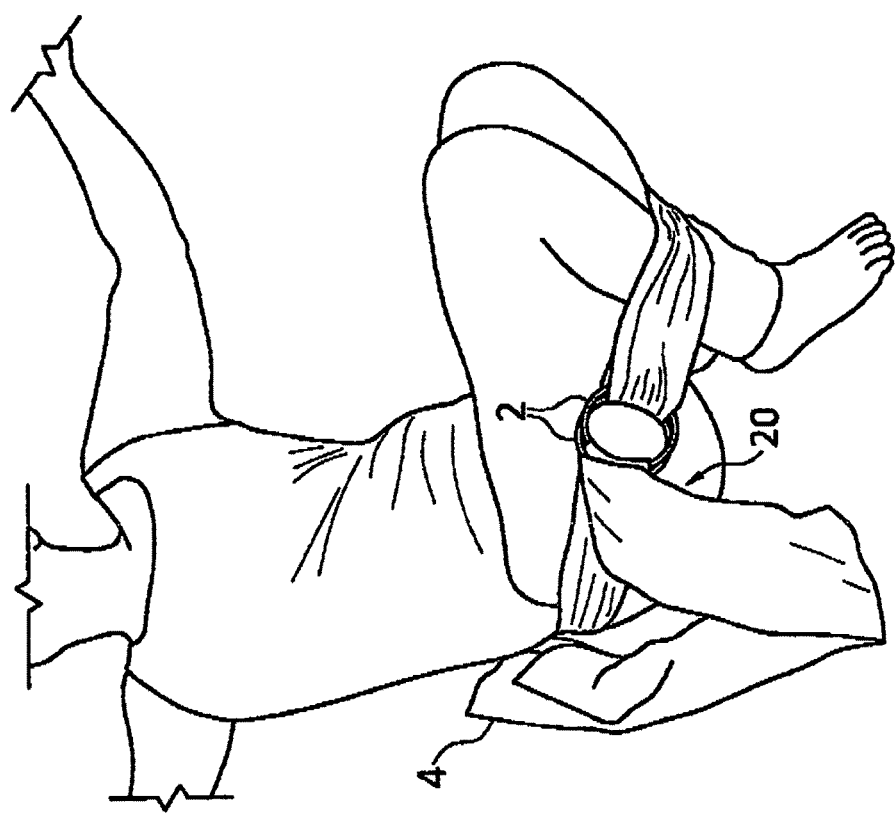

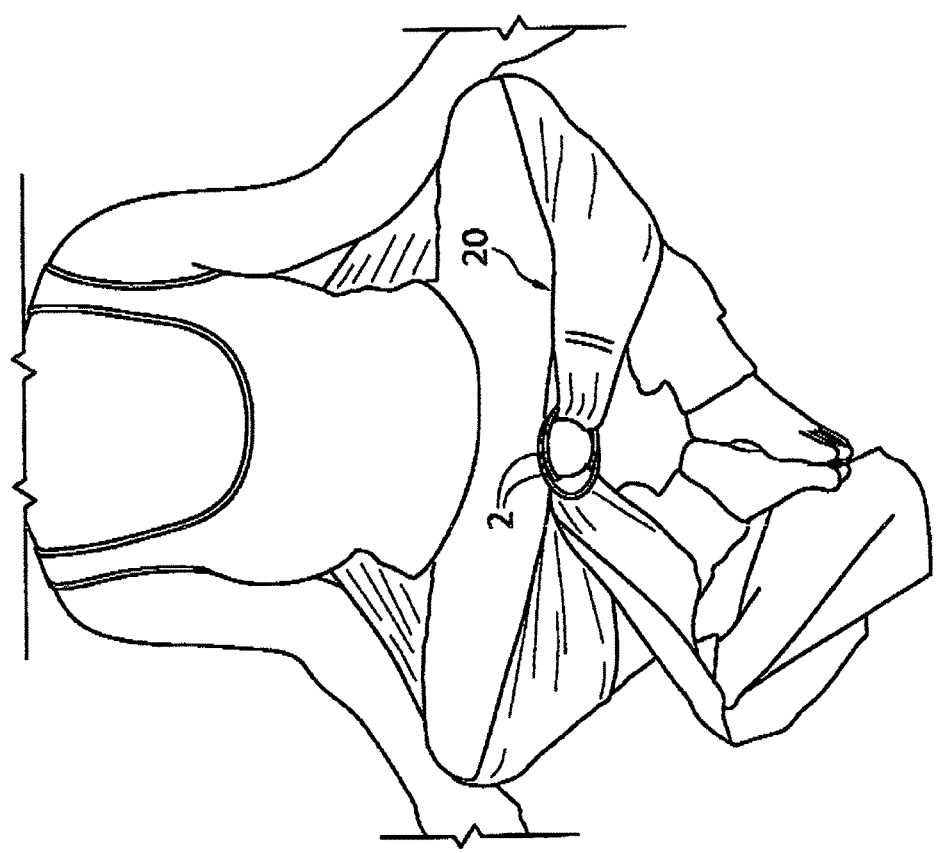

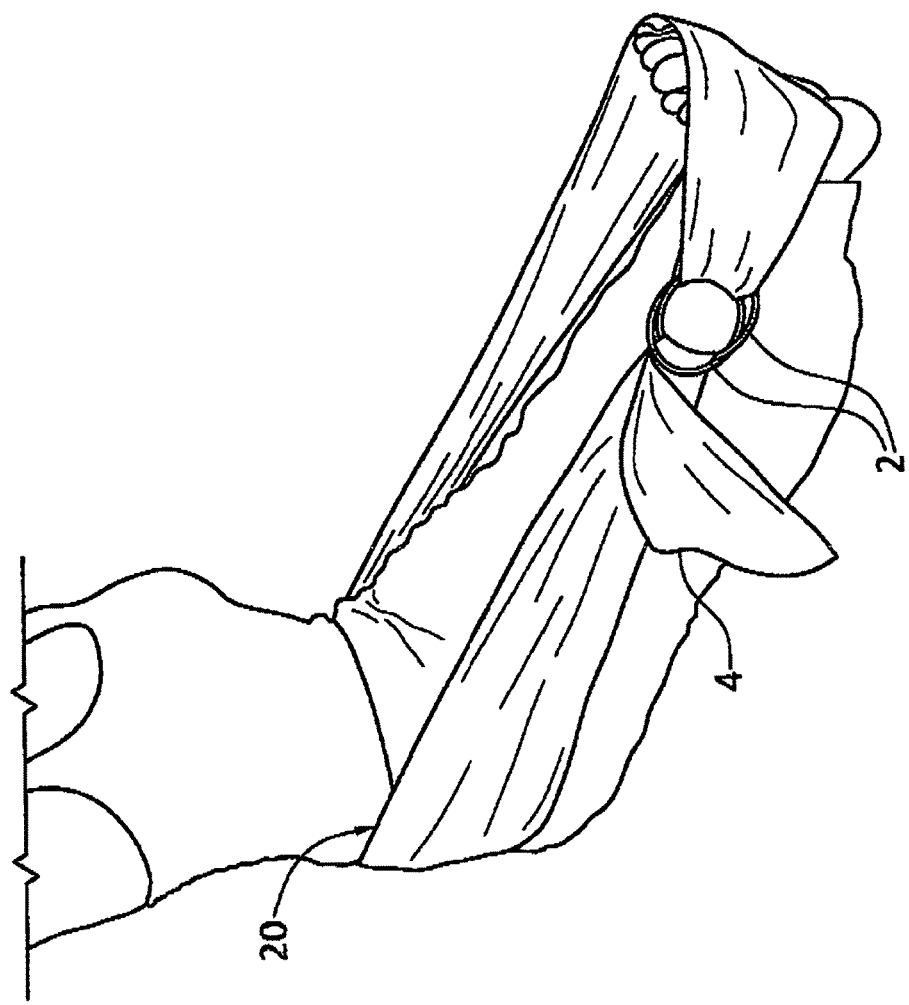

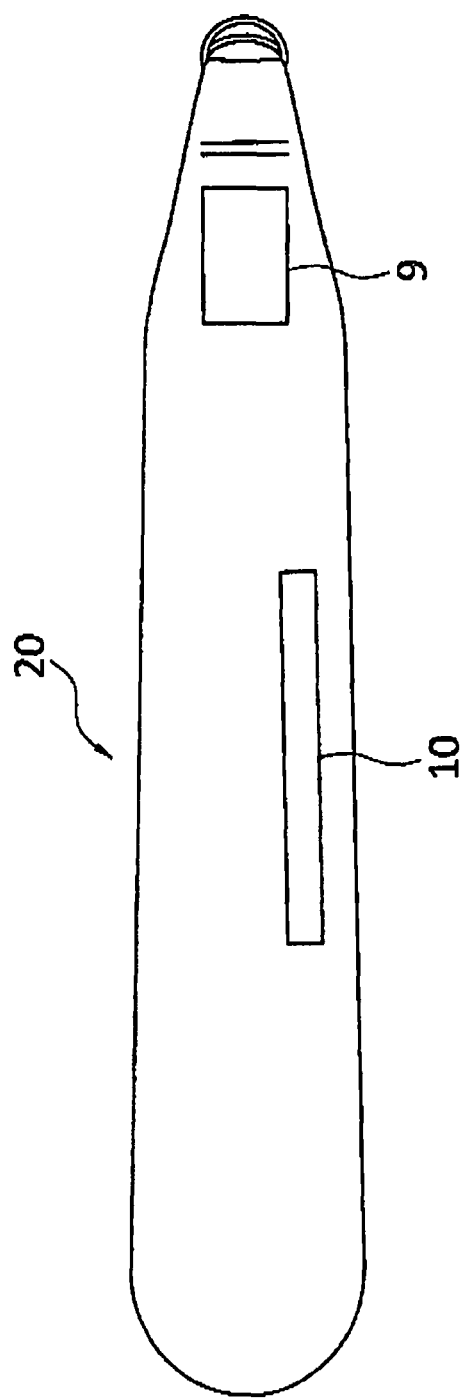

CLOTH BACK SUPPORT APPARATUS AND METHODS OF USE

BACKGROUND OF THE INVENTION

1. Field of the Invention

Meditation is the practice of mindfully observing one's thoughts, emotions, and the physical body. Most often meditation is practiced while sitting with the legs crossed and maintaining a straight spine.

Practitioners often complain about discomfort felt when sitting in the aforementioned posture, however this posture is the most conducive to meditation. Some practitioners argue this posture prevents one from obtaining a deep and mindful practice due to physical distraction and frustration.

The goal of meditation is to move beyond the attachment to thought and simple observation of the mind. Practitioners find difficulty in achieving such states of awareness when the physical body feels taxed. The mind becomes attached to the physical pain and therefore cannot move to simple observation of the experience and associated emotions.

2. Description of the Prior Art

Many known meditation aids unfortunately are rigid, hard and/or stationary. Thus, many are only useful when practicing in a designated location (IE the user's home or sanctuary,) as they do not readily travel or are cumbersome.

In addition, these aids are useful for sitting in only one or two position. Such are described, for example, in U.S. Pat. Nos. 7,628,455 and 3,890,004. In operation, the prior art requires a stable surface and does not transport easily. Other apparatus's such as U.S. Pat. Nos. 8,590,974 B2 and 4,394,049 are comprised of rigid materials and thus can be used in only one position. The present invention is compact, soft and flexible in nature.

Many known portable back support apparatus's exist, however are complex or tangle easily. Such are described, for example, in U.S. Pat. Nos. 5,643,184 and 5,001,791. In operation, the prior art is complex to figure out and the straps tangle easily.

There remains a need for a soft, flexible and easy to use portable back support.

SUMMARY OF THE INVENTION

The present invention was devised during a silent meditation retreat in which the inventor sat in meditation for 10 hours per day for 10 days. The present invention is a length of cloth consisting of a tail, body and buckle; the tail and buckle join to form a loop inside which a user sits. The apparatus and method of use stabilize a user in a seated position. The method of use is as follows: the cloth is wrapped around the user's back and knees while in a seated, crossed leg position, and the tail threaded through the buckle and cinched tight in front of the users body. The apparatus is adjusted by pulling the tail further through the buckle, increasing support, or pulling the buckle away from the user's body releasing tension.

The present invention relates to a back support apparatus for supporting a user's mid to low back, and a methodology for a user to sit in a simple cross-legged position, while supporting the spine following proper placement of the present invention around a user's back.

The present invention and method aids a user in achieving a comfortable seated position with proper placement of the apparatus around a user's back and knees as shown in the figures. The practitioner's knees are either down towards the ground or up in a more relaxed position, or other variations known to persons skilled at sitting for long periods of time. The apparatus is worn flat to cover the entire upper and mid back range, or folded, scrunched, knotted or twisted providing a more focused area of support and placed along any part of the spinal range of the upper, mid or low back. The present invention provides an easy and transportable apparatus with a simple method of obtaining a comfortable seat.

The preferred embodiment of the present invention along with a methodology of use is to aid a practitioner sitting in meditation or a user attending concerts, festivals, the beach, a park, camping or other activities where a user requires additional back support. The present invention is used as a method to obtain physical support of the lower lumbar spine and mid back so a user may enjoy a deeper meditative experience or the outdoors in comfort.

It is an object of the present invention and method to provide back support and comfort to a practitioner of meditation while seated with crossed legs. Further, the present invention and method accommodate a variety of users, from novice to advanced practitioner and most body shapes and sizes.

In addition, the present invention and method act as a physical support to a practitioner of yoga.

The present invention and method functions as a hip opener in prenatal care to prepare a user's body for child birth.

Additionally, the present invention may be used to carry a yoga mat.

It is another object of the present invention to provide an easily transportable unit which is used in a variety of atmospheres and settings. The present invention's method of use is supporting a practitioners' physical body in meditation, be it at home, the park, a meditation center or yoga studio.

It is a further object of the present invention to provide an easily transportable unit which provides comfort and back support to a user sitting at festivals, concerts, the park, beach, camping or any location a user may sit with the spine unsupported.

The present invention is a cloth apparatus (20) having a buckle at the first end (2) and a tail at the second end (4). The cloth is comprised of woven or knit fibers containing little to no stretch, such as but not limited to: cotton, linen, recycled polyester, hemp and may contain lycra, spandex or elastin.

In the preferred first embodiment of the present invention the apparatus is buckled together using two circular rings. The buckle may alternately be comprised of a conventional buckle, 'D' shaped rings or rectangular hardware, however are not restricted to the aforementioned.

The present invention is secured around a user in a crossed leg position by pulling the tail through the buckle, placing the loop around a user's knees and back, encircling the lower body and tightening the back support by pulling the tail end further through the buckle.

The present invention derives strength from folds in the cloth and securing the buckle to the body with reinforced stitching, however the buckle may be secured in other embodiments with latches, fasteners, locking snaps, however is not limited to the aforementioned; and in other embodiments the cloth remains unfolded prior to securing the buckle the length of cloth.

The preferred method of use of the present invention is aiding a practitioner of meditation in sitting with crossed legs and a straight spine. The apparatus is used alone or in conjunction with other meditation props, such as bolsters, blocks or cushions.

The first embodiment of the present invention uses the back support apparatus to aid a practitioner of meditation in achieving a comfortable seat while maintaining proper posture through correct placement of said apparatus upon a user's back and knees while sitting as shown in the Figures. The practitioner forms a loop with the apparatus which encircles the users' back and knees while seated with crossed legs. This is accomplished by weaving the tail through both buckles and then back through the furthest ring only. The user pulls the tail to form the desired loop size inside which to sit and places the formed loop on the surface of which to sit with the buckle in front of the body and proceeds to sit inside the loop in a crossed legged position using both hands to place the cloth across the back and around the knees. The knees act as a fulcrum point placing tension upon the cloth around the practitioner's back and pulling the spine into proper alignment. The cloth is adjusted vertically up or down a user's knees, which equally translates to the pressure upon a user's back. The apparatus may be worn flat covering the entire low to mid back range; or folded, scrunched, knotted or twisted providing a more focused area of support. Due to the present inventions ease of use and little to no elasticity, a practitioner is provided with a simple way to properly align the spine without a great deal of adjustment.

The second embodiment of the present invention uses the apparatus as described to obtain a comfortable seat while a user attends festivals, concerts or an event where a user must sit upon a surface with the spine unsupported. Such surfaces include but are not restricted to: the ground or floor, a meditation cushion, a block, bolster, cushion, a backless bench, bleachers or stool.

The third embodiment of the present invention aids a user in supporting the body when using the apparatus as described for prenatal care. The apparatus supports a user while seated with crossed legs or with the soles of the feet together in butterfly pose assisting the body in preparation for natural childbirth by pushing the uterus forward and stretching the cartilage and ligaments at the sacroiliac joints and front of the symphysis pubis bone which open the pelvis and stretch the legs.

The fourth embodiment of the present invention demonstrates a practitioner using the apparatus as described when practicing yoga. Such yoga postures in which to use the present invention and method include, but are not limited to: sitting with crossed-legs (sukasana, lotus pose, easy pose), butterfly pose, reclining butterfly pose, spinal twist with bent knees, seated forward fold with legs outstretched, knees to chest and other variations as would be known to a person skilled or knowledgeable in the art of yoga or stretching, and the latter postures as known by any other names.

The fifth embodiment of the present invention describes a user wearing the apparatus as a scarf. The present invention is worn as a scarf to keep a user warm. A user wears the present invention as a scarf by weaving the tail through the buckle 4-10" and looping the cloth around a user's neck 1 or more times depending on the users desired level of comfort.

The sixth embodiment of the present invention describes a user wearing the apparatus as a shawl. The present invention is worn as a shawl to protect a user's skin from sun or to keep warm. A user wears the present invention as a shawl by draping the cloth over the shoulders then securing the tail end through the buckle and tightening to maintain placement.

The seventh embodiment of the present invention includes a pocket to support an iPod or other audio device such as, but not limited to, a smart phone, iPod or iPhone to listen to guided meditations or music while using the apparatus as described in any of the previous embodiments. The present invention's pockets are placed at the inventors' discretion.

The eighth embodiment of the present invention is fabricated from cloth material as described above in multiple layers and contain pockets or placements for hot or cold therapy packs, healing stones, gems, aromatherapy packs, herbal packs and poultices or other healing aids.

The ninth embodiment of the present invention is a method for carrying a yoga mat. The tail of the apparatus is threaded through the buckle leaving a small circle which is placed around one end of a rolled up yoga mat and the cloth is cinched tight. The tail of the apparatus is then tied around the opposite end of the rolled up yoga mat. This creates a strap which a user can wear over one shoulder or slung across the back.

BRIEF DESCRIPTION OF THE DRAWINGS

FIG. 5 Illustrates the method of use in the second embodiment of the present invention while sitting at a festival, concert or other event where the user is seated on a surface without back support.

FIG. 6B Illustrate a method of use of the present invention in the fourth embodiment when performing yoga postures, and the third embodiment in prenatal care. Two-knee twist pose.

FIG. 6D Illustrate a method of use of the present invention in the fourth embodiment when performing yoga postures, and the third embodiment in prenatal care. Seated butterfly or baddha konasana pose.

FIG. 6E Illustrate a method of use of the present invention in the fourth embodiment when performing yoga postures, and the third embodiment in prenatal care. Staff pose, forward fold, life nerve stretch.

FIG. 7 Shows an illustration of the present invention (20) with pockets or sleeves.

DESCRIPTION OF THE PREFERRED EMBODIMENTS

Figure 1A:
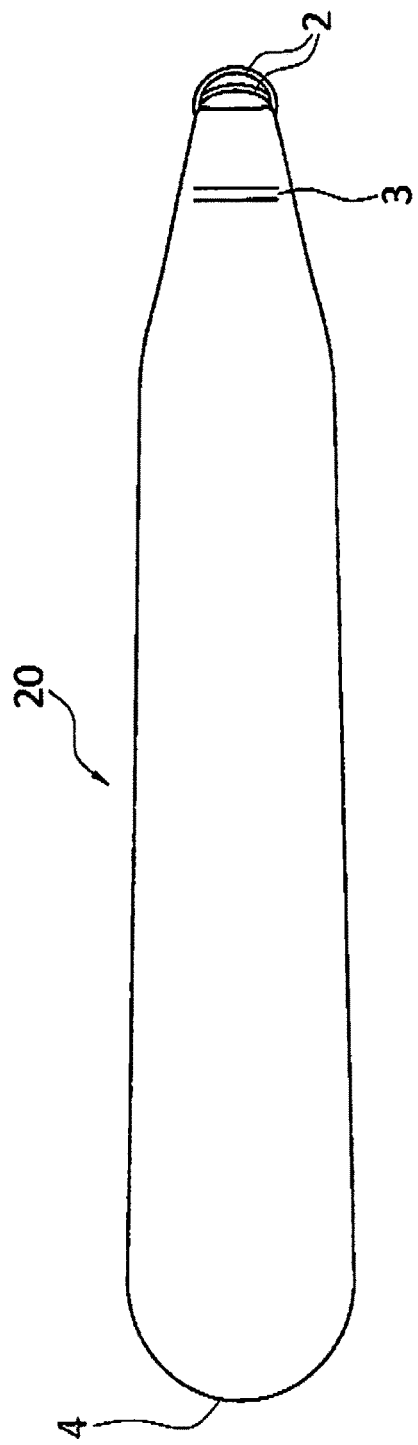
FIG. 1A Right side view of the present invention (20) having a buckle at the first end (2) and a tail at the second end (4).

The following description should be read with reference to the drawings, in which like elements in different drawings are numbered in like fashion. The drawings which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

The drawings in FIGS. 1A, 1B, 2A, 26, 3A, 3B, 3C, 3D, 3E and 4A, 4B, 4C, 4D and 4E illustrate the preferred first embodiments of the present invention.

The present invention as shown in FIGS. 1 through 10 is an apparatus (20) consisting of a length of cloth having a first buckle end (2) and a second tail end (4). The buckle is securely fastened with reinforced stitching (3) at the first end. For the purposes of this document, the buckle will be depicted as 2 circular rings (2) secured to the first end with two rows of reinforced stitching (3).

Alternately, the buckle (2) of the present invention (20) may be constructed of materials such as, but not restricted to, metal, nylon or plastic, in a round, oval, square, oblong or 'D' shapes and in varying sizes and quantities, which those skilled in the art will see as a suitable alternatives.

Alternately, the buckle (2) of the present invention (20) may be secured by way of locking fasteners, snaps, latches or other secure locking mechanism those skilled in the art will recognize as suitable alternatives.

Figure 1B:
FIG. 1B Back view of the present invention (20) having a buckle at the first end (2) and a tail at the second end (4).

Referring now to FIGS. 1A and 1B, which illustrate the basic layout of the first embodiment of the present invention (20) showing the tail end (4), buckle (2) and means of securing the buckle (3). The present invention (20) is shown from the front in FIG. 1A, and from the back as shown in FIG. 1B. FIG. 1B details the folds of the cloth (5) in the preferred first embodiment of the invention.

Figure 2A:
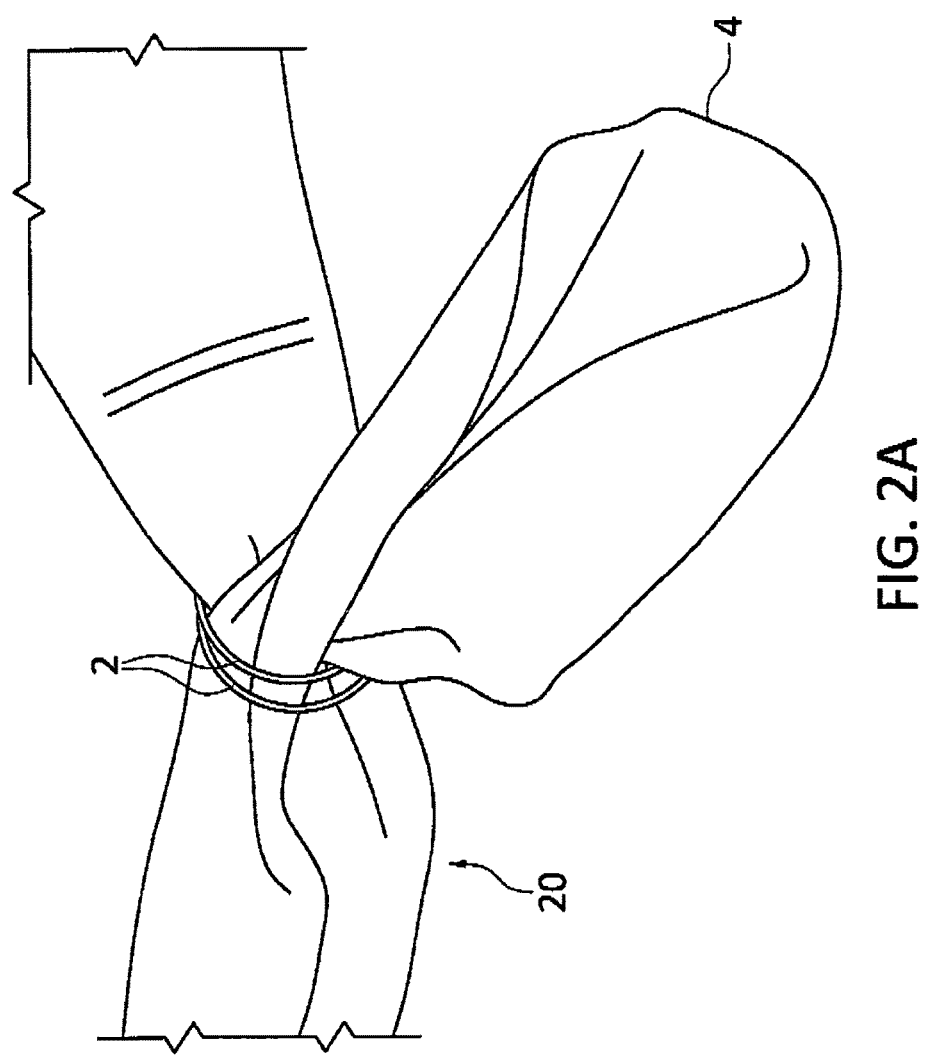
FIG. 2A Shows step one of the present invention (20) being secured by weaving the tail (4) through both buckles (2).
Figure 2B:
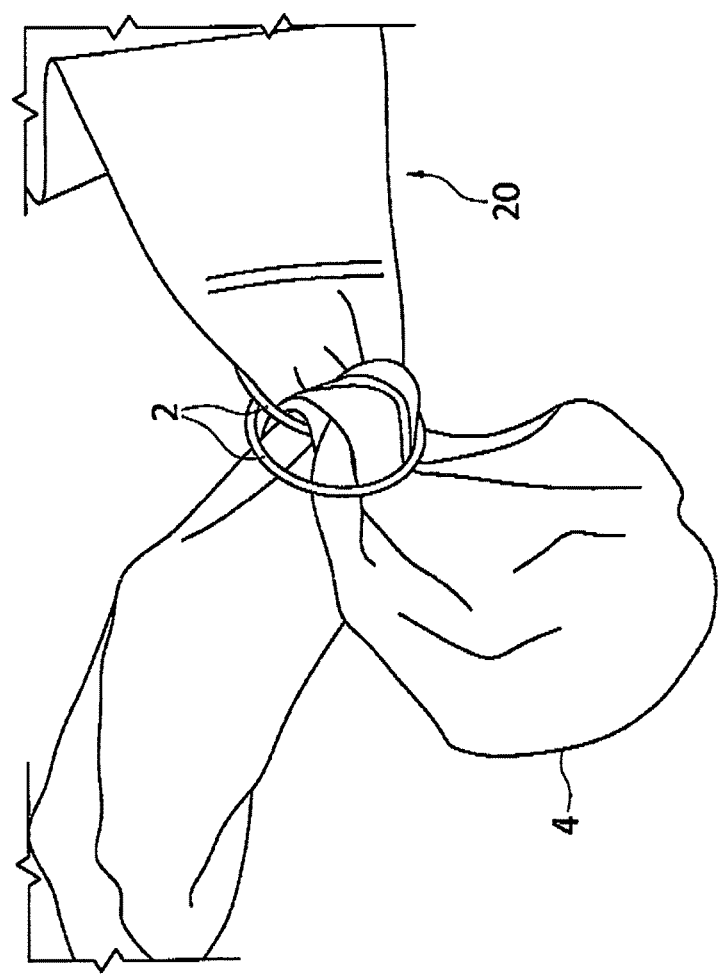
FIG. 2B Shows step two of the present invention (20) being secured by weaving the tail (4) over the closest buckle then through the furthest buckle (2) only.

Referring now to FIGS. 2A and 2B, which detail the preferred first embodiment of the present invention's means of closure via a buckle (2) comprised of 2 circular rings. The figures detail a two-step process of securely fastening the apparatus (20). First weave the cloth tail through both rings (2) as shown in FIG. 2A, then weave the tail through the furthest ring (2) only as shown in FIG. 2B. Pulling the tail (4) adjusts the loop size and tension upon a user's body.

Figure 3A:
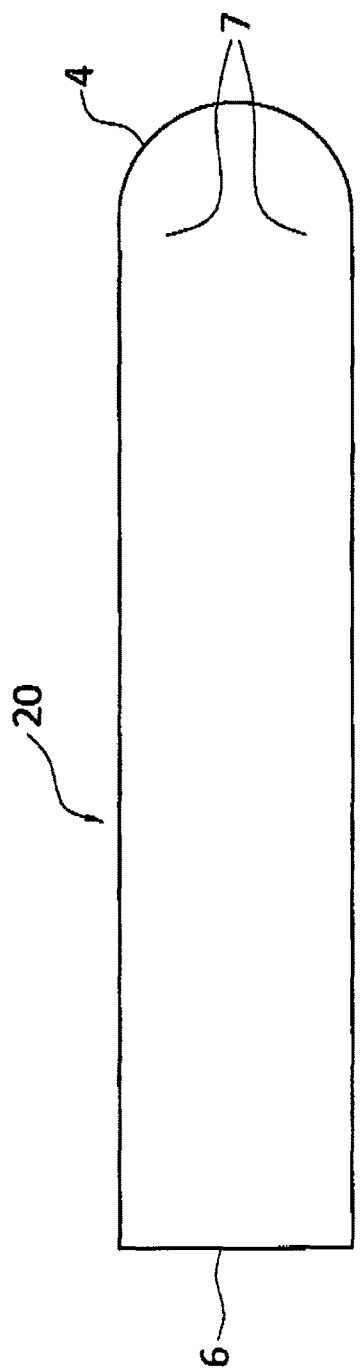
FIG. 3A Shows the present invention's (20) plan view of one method of manufacturing. This view shows the cloth in its first cut stage with a rounded tail (4), squared end (6) and 2 fold lines (7).
Figure 3C:
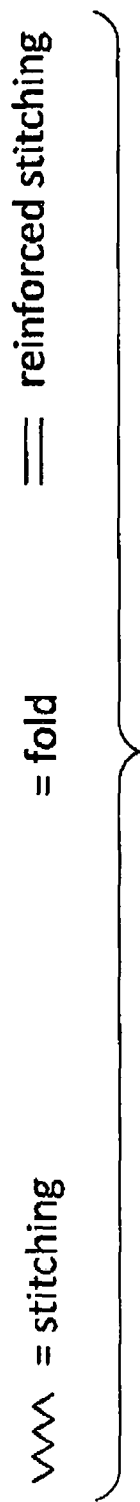
FIG. 3C Legend for the present invention's (20) plan view of one method of manufacturing. This view shows stitch marks, fold lines and secure/reinforced stitching.
Figure 3D:
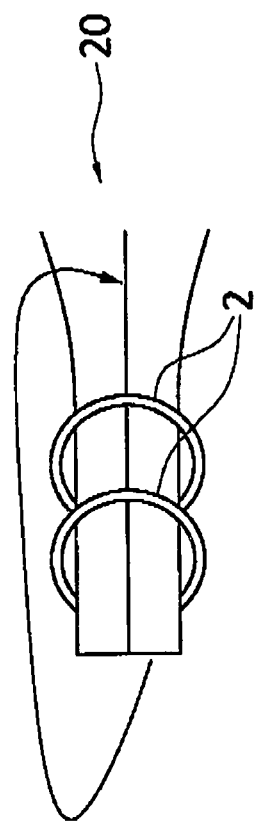
FIG. 3D Shows the present invention's (20) plan view of one method of manufacturing. This view shows the folded cloth inserted through the two rings (2) and folds over said rings as indicated by the arrows.
Figure 3E:
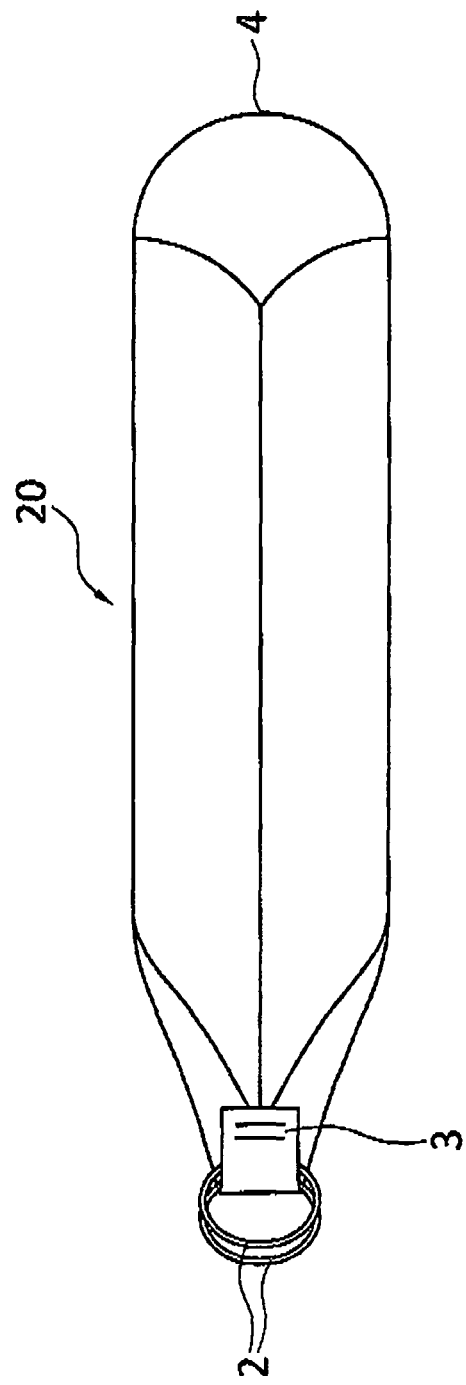
FIG. 3B Shows the present invention's (20) plan view of one method of manufacturing. This view shows cloth folded into the center point and stitched together at the squared end. Two additional marks indicate where the sides fold again towards the center line (8).
FIG. 3F Shows the present invention's (20) plan view of one method of manufacturing. This view shows the cloth folded over, and the rings (2) stitched securely into place with a double line of reinforced stitching (3). This is the basic layout of the first embodiment of the present invention (20).

Referring now to FIGS. 3A through 3E, a series of plan views which illustrate the steps required to produce the present invention (20) in its preferred first embodiment (FIGS. 1A and 1B). FIG. 3A shows the cloth in its first cut stage with a rounded tail (4), squared end (6) and 2 fold lines (7). FIG. 3B shows the cloth folded into the center point and stitched together at the squared end. Two additional marks indicate where the sides fold again towards the center line (8). FIG. 3C is a legend for stitch marks, fold lines and secure/reinforced stitching. FIG. 3D shows the folded cloth inserted through the two rings (2) and folds over said rings as indicated by the arrows. FIG. 3E shows the cloth folded over, and the rings (2) stitched securely into place with a double line of reinforced stitching (3). This is the basic layout of the first embodiment of the present invention (20).

Figure 4A:
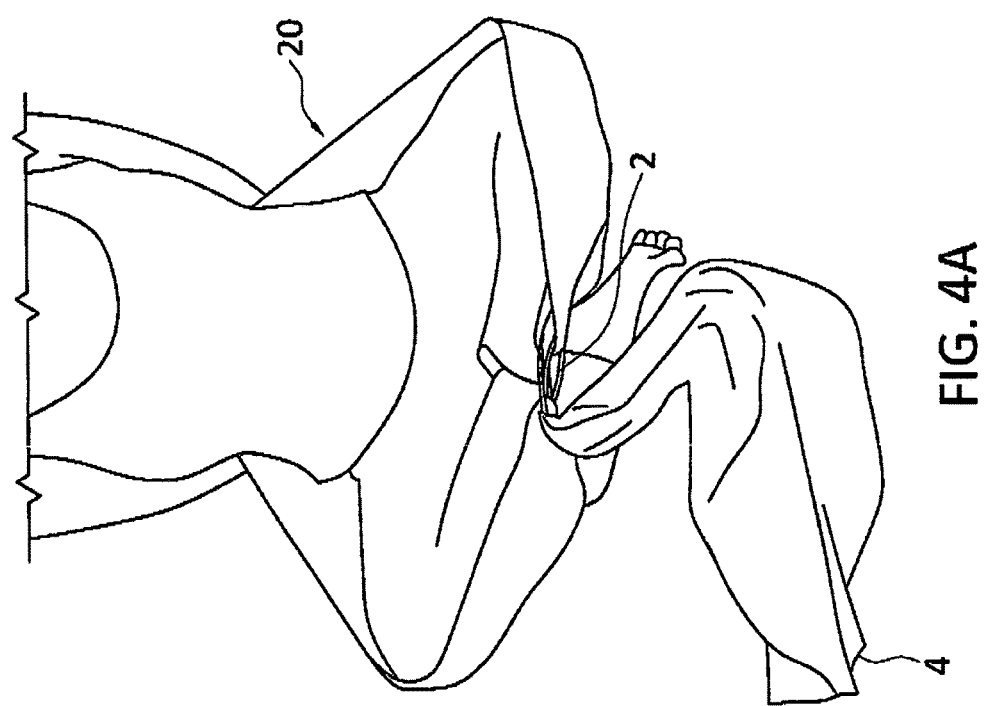
FIG. 4A Shows a preferred first embodiment of the present invention (20) when sitting with crossed legs.
Figure 4B:
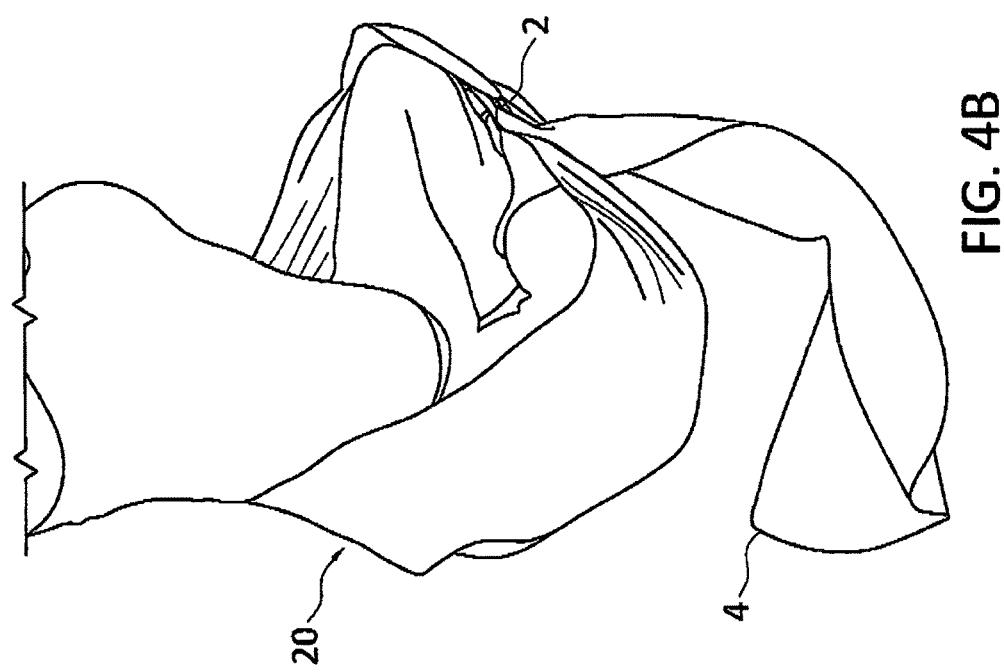
FIG. 4B Shows the side view of the present invention (20) in a preferred first embodiment when sitting with crossed legs.
Figure 4C:
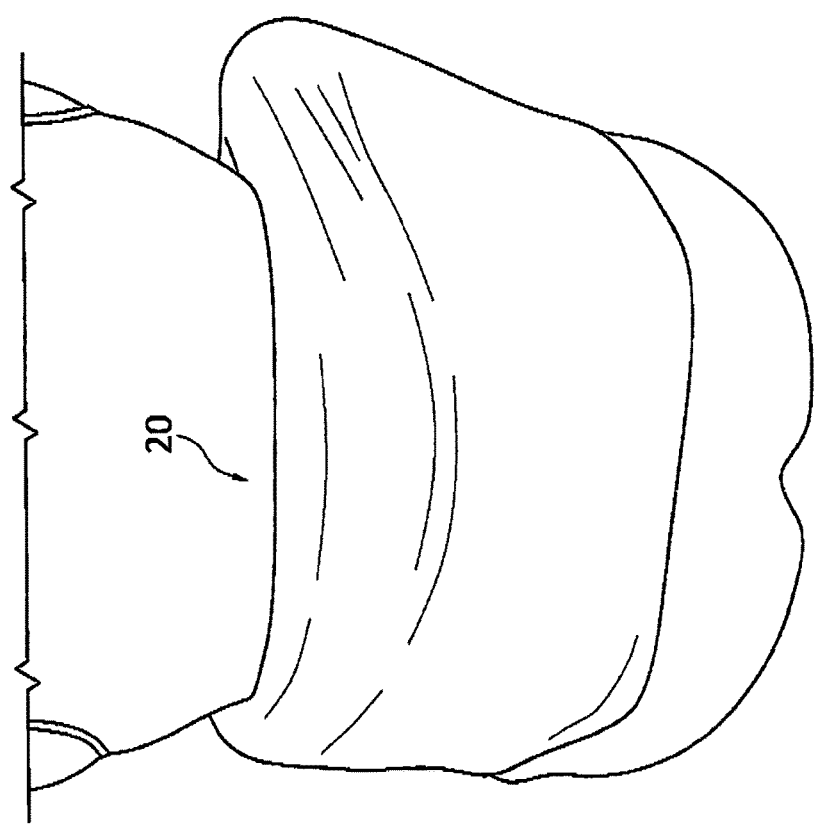
FIG. 4C Shows the fabric flat across the back in a preferred first embodiment of the present invention (20) when sitting with crossed legs.
Figure 4D:
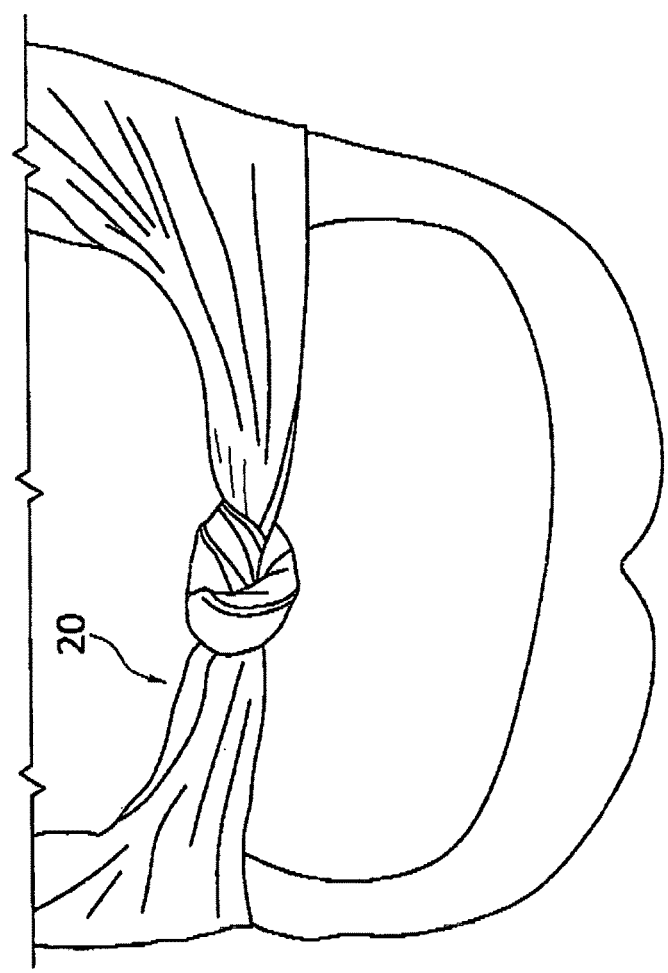
FIG. 4D Shows the fabric knotted at the back in a preferred first embodiment of the present invention (20) when sitting with crossed legs.
Figure 4E:
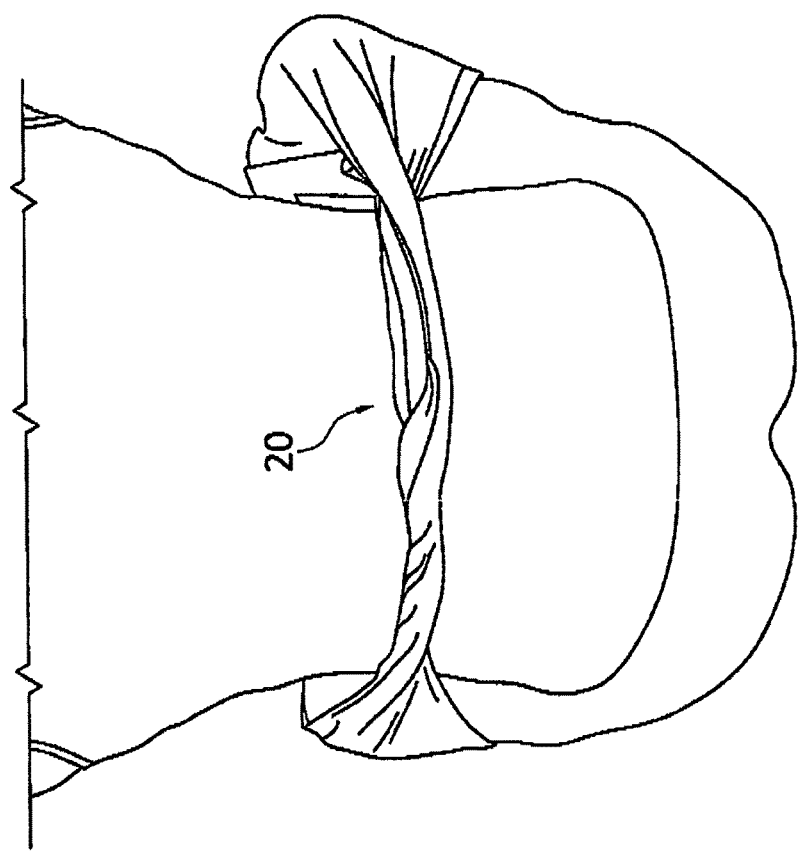
FIG. 4E Shows the fabric twisted at the back in a preferred first embodiment of the present invention (20) when sitting with crossed legs.

The following refers to FIGS. 4A and 4B in the first embodiment of the present invention (20) as a method used to sit in meditation. The tail end (4) is woven through the buckle (2), then loops back and is threaded through the furthest ring only (2) (FIGS. 2A and 2B). A user pulls the tail (4) to form the desired loop size inside which to sit. The user places the formed loop on the surface of which to sit with the buckle (2) in front of the body and proceeds to sit inside the circular loop in a crossed legged position using both hands to place the cloth across the users back and around the knees. A user pulls the tail end (4) which places tension upon the cloth around the knees and back, pulling the cloth closer but not tight. A user then lifts up the knees a few inches while pulling the tail end (4) through the buckle (2), allowing the loop to further envelop the body, then relaxes the knees down and further adjust the cloth over the knees. Pulling the cloth up or down at the knees directly affects the tension felt across the back. FIGS. 4A and 4B illustrate a straight spine conducive to meditation.

The back support apparatus (20) is worn flat across the back to cover the entire low to mid back range (FIG. 4C), or is knotted (FIG. 4D), twisted (FIG. 4E), folded or scrunched to provide a more focused area of support which is placed at any point on a user's back. The user adjusts the cloth across the back finding a comfortable placement of pressure before relaxing into the final posture which has pulled the spine into proper alignment.

Referring again to FIGS. 4A and 4B wherein the invention (20) is used as an aid and method for supporting the body in prenatal care in the third embodiment. The crossed leg posture pushes the uterus forward, stretches the legs and opens the pelvis by stretching the cartilage and ligaments at the sacroiliac joints and the front symphysis pubis bone allowing the pelvic cartilage and ligaments to relax and open.

Referring now to FIG. 5, the method of use in the second embodiment of the present invention (20) at concerts, festivals, the beach, park, camping or other activity where a user is seated with the back unsupported. A user creates a loop with the apparatus and proceeds to sit inside said loop as shown in the Figures. A user then maneuvers the cloth apparatus (20) across the back and around the shins while the knees are bent, bringing them in towards the chest and torso (FIG. 5). The shins act as a fulcrum placing tension upon the cloth apparatus (20) around a user's back, supporting a comfortable and relaxed upright position. A user pulls the tail end (4) through the buckle placing tension upon the cloth around the back and envelops the body. The back support apparatus (20) may be worn flat across the users back (FIG. 4C), knotted (FIG. 4D), twisted (FIG. 4E, folded or scrunched. The user then relaxes the knees and back into the cloth finding a comfortable position.

Figure 6A:
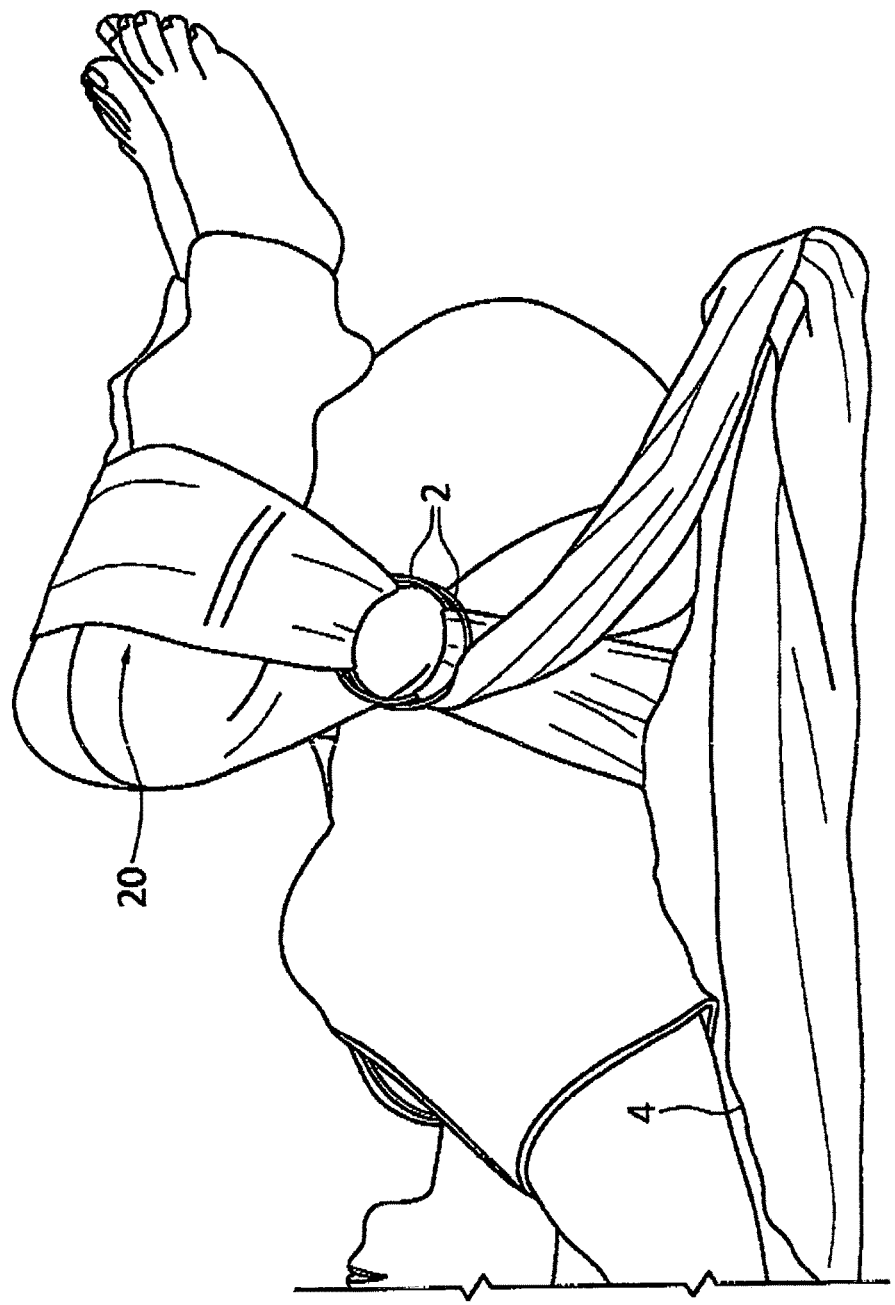
FIG. 6A Illustrate a method of use of the present invention in the fourth embodiment when performing yoga postures, and the third embodiment in prenatal care. Knees to chest pose.

Referring now to the present invention (20) when used as a method for the fourth embodiment as an aid to practice yoga postures as illustrated in FIGS. 6A through 6E. FIG. 6A shows a practitioner in the knees to chest position, wherein the user lies in a supine position placing the looped cloth apparatus (formed using the instructions detailed above) under the mid back and pulls the knees to the chest through the loop. A user's body is encased within the loop and the buckle (2) is on the left or right side of the user's body between the knees and chest. The buckle (2) is then cinched tight by pulling the tail end (4) and the user relaxes the body.

Referring now to FIG. 6B which shows the present invention (20) used as a method to practice the yoga posture: spinal twist with knees to chest. A user begins with the knees to chest in a supine position, then slides the apparatus (20) from the back to under the hips, and from the knees to the mid shin. The apparatus (20) is then tightened with the buckle (2) which comes to rest on the side of the practitioner's legs, in the space between the thigh and calf so as not to pinch a user's skin once twisted. A user then allows the knees to fall to the side of the body in a twist, stretching the opposite side of the torso.

Figure 6C:
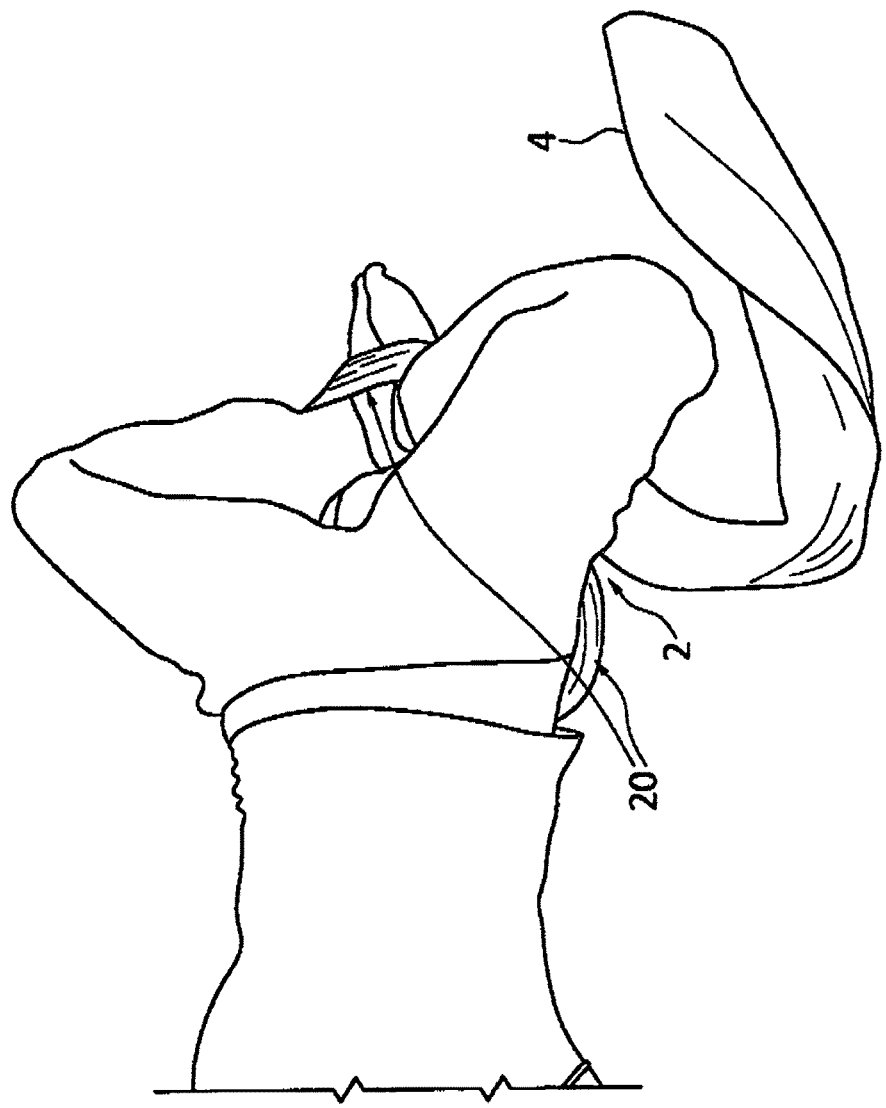
FIG. 6C Illustrate a method of use of the present invention in the fourth embodiment when performing yoga postures, and the third embodiment in prenatal care. Reclined butterfly or supine baddha konasana pose.

Referring now to FIG. 6C which shows the back support apparatus (20) used as a method to practice the yoga posture: reclined butterfly. A user lies supine with the knees to chest, and slides the back support apparatus (20) from the back to under the hips and from the shins to the ankles. The user pulls the tail (4) of the apparatus (20) to a comfortable tension and brings the feet to the floor just beyond the buttocks with the knees bent. A user then allows each knee to fall out towards the sides leaving a large diamond shaped space between the groin and legs with the soles of the feet touching. A user's inner thigh and groin muscles are stretched.

Referring now to FIG. 6D which shows the back support apparatus (20) used as a method to practice yoga in the butterfly position of the fourth embodiment. A user sits inside the back support apparatus (20) formed into a loop with the buckle in front. The user sits with the soles of the feet together and the knees out to the sides, creating a diamond shaped space between the heels and groin. A user then places the cloth apparatus (20) across the mid back area and over the knees. The buckle (2) is tightened and a user relaxes into the position allowing the back to be supported.

Referring again to FIG. 6D which shows the back support apparatus (20) used as an aid and method for supporting the body in prenatal care as outlined in the third embodiment detailing the present inventions use in preparation for a natural birth. The posture pushes the uterus forward, stretches the legs and opens the pelvis by stretching the cartilage and ligaments at the sacroiliac joints and the front symphysis pubis bone allowing the pelvic cartilage and ligaments to relax and open.

Referring now to FIG. 6E which shows the back support apparatus (20) used as a method to practice yoga in a forward fold position. A user sits inside the looped apparatus above, with the legs straight out in front of the torso. The looped apparatus is placed around a user's hips and the balls of the user's feet. The buckle (2) is tightened with the tail (4) so the user's feet are supported in a flexed position which stretch the muscles of the backs of the legs. A user may remain in this position while sitting with a straight spine or begin folding forward from the hips.

Referring now to FIG. 7, which illustrates the present invention (20) having pockets (9) for an audio apparatus, keys, cards, healing stones or crystals and/or sleeves (10) for therapeutic packs or poultices. An embodiment may contain none or all of the aforementioned in any arrangement. An embodiment with pockets (9) or sleeves (10) may be comprised of two or more layers of cloth to create pockets (9) by slicing and stitching; however cloth pockets (9) or sleeves (10) may be sewn onto the preferred first embodiment (20). When the cloth is doubled, FIG. 3A is altered so that it mirrors itself, essentially doubling the pattern and stitched together.

The present invention comprised of pockets (9) or sleeves (10) for therapeutic packs may further be comprised of a zipper, Velcro, press seal closure, cloth flap for closure. The pockets (9) and sleeves (10) may be rectangular, square, oblong, round and various sizes are placed along or across the sling and in any quantity, size and/or shape.

Figure 8:
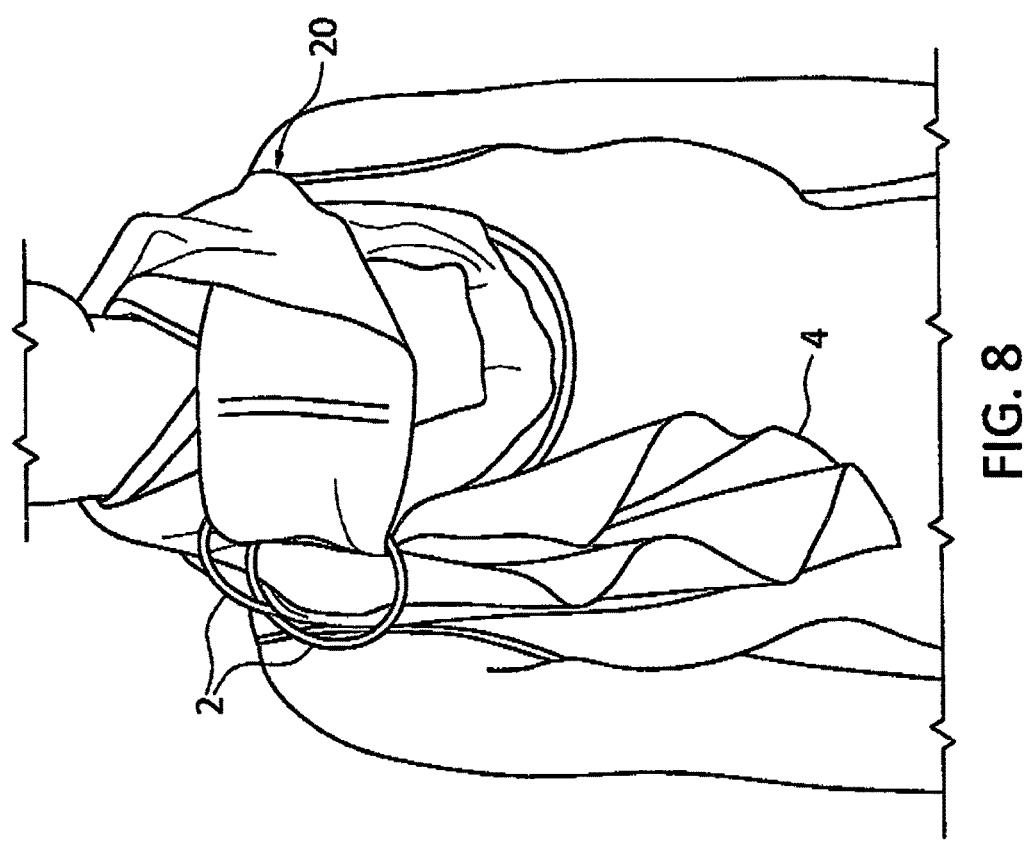
FIG. 8 Illustrates the present invention (20) worn as a scarf.

Referring now to FIG. 8 which illustrates the present invention (20) worn as a scarf to keep the user warm. The apparatus worn as a scarf by weaving the tail end (4) through the buckle (2), approximately 4-6" and looping the cloth around a user's neck 1 or more times depending on the users desired level of comfort.

Figure 9:
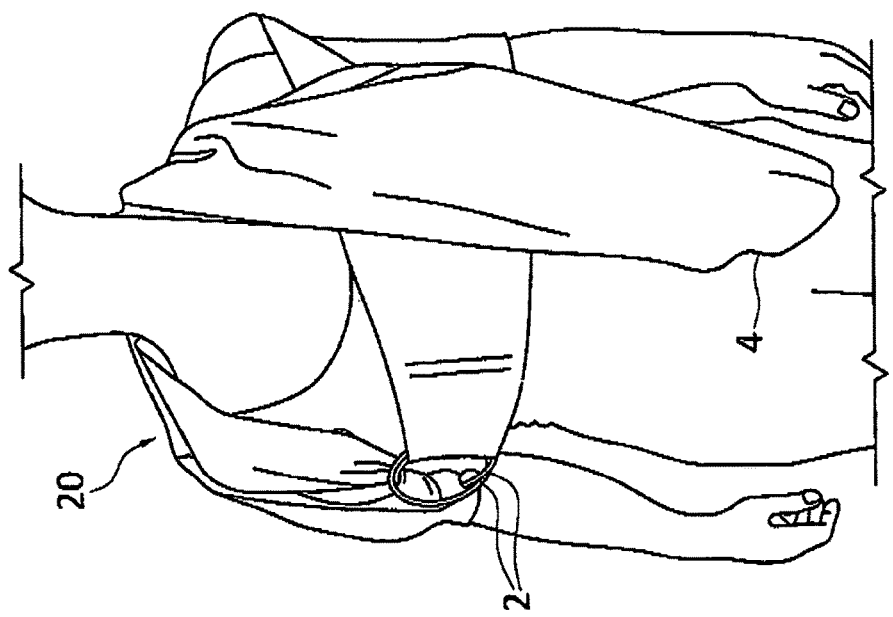
FIG. 9 Illustrates the present invention (20 worn as a shawl.

Referring now to FIG. 9 which illustrates the present invention (20) worn as a shawl to keep the user warm and provide sun protection. The apparatus is draped over a user's shoulders and secured by pulling the tail end (4) through the buckle (2).

Figure 10:
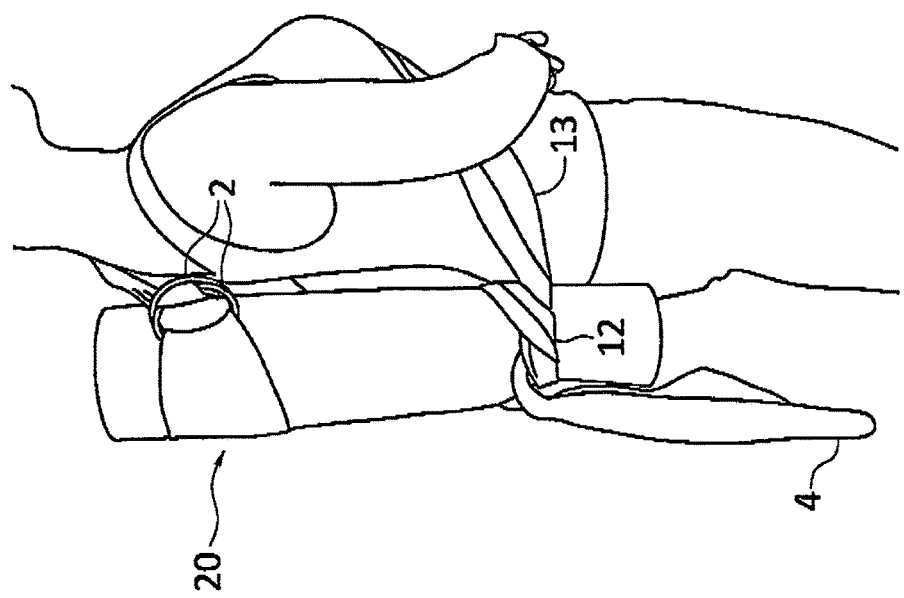
FIG. 10 Illustrates the present invention (20) used to carry a yoga mat.

Referring now to FIG. 10 which shows the present invention (20) used as a method to carry a yoga mat. The tail (4) passes through the buckle (2) forming a small loop which is placed around one end of the rolled up yoga mat. The tail is then tied (12) around the opposite end of the yoga mat. This creates a strap (13) which can now be worn over a user's shoulder or slung across a user's back.

The embodiments of the invention in which an exclusive property or privilege is claimed are defined as follows:

1. A method for maintaining a user in a desired seating position, the method comprising:
    providing a back support apparatus comprised of a reinforced length of cloth with a first end provided with a buckle and a second end adapted to be threaded through the buckle, wherein the cloth measures 2.5 meters in length and 41 centimeters in width;
    wrapping the cloth around a substantial portion of the lower lumbar region of a back of a user;
    threading the second end through the buckle such that the cloth forms a loop;
    positioning the user's knees within and against the loop such that tension is placed on the cloth; and
    pulling the second end through the buckle such that the loop is tightened around the back and knees of the user so as to maintain the user in the desired seating position with the reinforced length of cloth supporting the back and knees of the user.

2. The method of claim 1 wherein the desired seating position is a cross-legged position and the reinforced cloth stabilizes the user as they maintain the cross-legged sitting position.

3. The method of claim 1 further comprising the step of placing the cloth flat against the lower lumbar region of the user's back.

4. The method of claim 1 further comprising the step of scrunching the clothing into folds against the lower lumbar region of the user's back to provide additional support and comfort to the user when maintaining a desired seating position.

5. The method of claim 1 wherein the cloth is fold over one or more times and placed against the lower lumbar region of the user's back to provide additional support and comfort to the user when maintaining a desired seating position.

6. The method of claim 1 wherein the cloth of the back support apparatus is positioned so as to cover a substantial portion of the back of the user when practicing yoga postures, enabling the user's muscles to relax more deeply into a supported pose.

7. The method of claim 1 comprising the step of positioning the cloth of the back support apparatus on the lower lumbar of the back to reduce muscle tension upon the knees and the user's back.

8. The method of claim 1 comprising the step of positioning the cloth of the back support apparatus on the mid-spine of the back to reduce muscle tension upon the knees and the user's back.

9. The method of claim 1 wherein the desired seating position is a crossed-leg or butterfly position allowing for loosening of the pelvic tendons and ligaments in preparation for a natural birth.

10. The method of claim 1, further comprising the step of using the back support apparatus as a scarf such that the reinforced length of cloth is looped around a user's neck and the second end is threaded through the first end and pulled to tighten the cloth as desired around the user's neck.

11. The method of claim 1, further comprising the step of using the back support apparatus, as a shawl such that the reinforced length of cloth is looped around a user's shoulders and the second end is threaded through the first end and pulled to tighten the cloth as desired around the user's shoulders.

12. The method of claim 1, further comprising the step of using the back support apparatus as a yoga mat carrying apparatus such that the reinforced length of cloth is looped around the rolled yoga mat and the second end is threaded through the first end and pulled to tighten the cloth around a rolled yoga mat.

* * * * *